United States Patent
Williams et al.

(10) Patent No.: US 6,314,311 B1
(45) Date of Patent: Nov. 6, 2001

(54) MOVABLE MIRROR LASER REGISTRATION SYSTEM

(75) Inventors: Gilbert T. Williams, Richmond Heights; James M. McNally, Montville, both of OH (US)

(73) Assignee: Picker International, Inc., Highland Heights, OH (US)

( * ) Notice: Subject to any disclaimer, the term of this patent is extended or adjusted under 35 U.S.C. 154(b) by 0 days.

(21) Appl. No.: 09/362,813

(22) Filed: Jul. 28, 1999

(51) Int. Cl.$^7$ ........................................................ A61B 6/00
(52) U.S. Cl. ................................ 600/425; 600/407; 345/7
(58) Field of Search ................................ 600/407, 425, 600/130, 473, 424, 427; 606/130; 348/77, 51; 345/7, 9

(56) References Cited

U.S. PATENT DOCUMENTS

| 5,309,913 | | 5/1994 | Kormos et al. . | |
|---|---|---|---|---|
| 5,383,454 | | 1/1995 | Bucholz . | |
| 5,526,812 | * | 6/1996 | Dumoulin et al. | 128/653.11 |
| 5,590,655 | | 1/1997 | Hussman . | |
| 5,772,593 | * | 7/1998 | Hakamata | 600/407 |
| 5,776,064 | | 7/1998 | Kalfas et al. . | |
| 5,792,147 | * | 8/1998 | Evans et al. | 606/130 |
| 5,921,992 | * | 7/1998 | Costales et al. | 606/130 |
| 5,978,696 | * | 11/1999 | VomLehn et al. | 600/411 |
| 6,038,467 | * | 3/2000 | De Bliek et al. | 600/424 |
| 6,161,033 | * | 12/2000 | Kuhn | 600/429 |

* cited by examiner

Primary Examiner—Marvin M. Lateef
Assistant Examiner—Eleni Mantis Mercader
(74) Attorney, Agent, or Firm—Fay, Sharpe, Fagan, Minnich & McKee, LLP

(57) ABSTRACT

A registration system (200) for use in connection with an image guided surgery system (10) is provided. It includes a medical diagnostic imaging apparatus (100) for collecting image data from a subject (310). An image data processor (130) reconstructs an image representation of the subject from the image data. An image projector (230) depicts the image representation on the subject (310). In a preferred embodiment, the image projector (230) depicts the image representation on the subject (310) such that registration between the subject (310) and the image representation is readily apparent. Preferably, the image projector (230) is a laser lightshow projector, a projection television, or a backlit liquid crystal display device. Optionally, a data processor (210) applies corrections to the image data such that surface contours of the subject (310) are accounted for when the image is projected onto the subject (310).

21 Claims, 3 Drawing Sheets

MOVABLE MIRROR LASER REGISTRATION SYSTEM

BACKGROUND OF THE INVENTION

The present invention relates to the medical diagnostic imaging and surgical arts. It finds particular application in conjunction with image guided surgery (IGS), and will be described with particular reference thereto. However, it is to be appreciated that the present invention is also amenable to other like applications.

Medical diagnostic imaging is a valuable tool for obtaining accurate visualization of a particular patient's internal anatomy and/or pathology in a minimally invasive manner. Prior to a medical procedure, three-dimensional (3D) diagnostic image data of the brain, spinal cord, and/or other anatomy of interest is often generated by computed tomography (CT) scanners, magnetic resonance imaging (MRI) scanners, gamma cameras, and other medical diagnostic imaging equipment. Typically, these imaging modalities provide structural detail with a resolution of a millimeter or better. Images, such as slices, 3D renderings, or projections, of the patient's anatomy are reconstructed and displayed on a video monitor and then used by medical personnel to aid in navigating through and/or around various anatomical structures. The displays are typically mounted displaced from the surgically sterile region surrounding the patient.

Various frameless stereotactic IGS procedures have been developed which take advantage of the 3D image data of the patient. These procedures include guided-needle biopsies, shunt placements, craniotomies for lesion or tumor resection, and the like. Another area of frameless stereotaxy procedure which requires extreme accuracy is spinal surgery, including screw fixation, fracture decompression, and spinal tumor removal.

In spinal screw fixation procedures, for example, surgeons or other medical personnel drill and tap a hole in spinal vertebra into which a screw is to be placed. The surgeon often relies heavily on his own skill in placing and orienting the bit of the surgical drill prior to forming the hole in the vertebra. Success depends largely upon the surgeon's estimation of anatomical location and orientation in the operative field. Unaided, this approach can lead to less than optimal placement of screws which in turn may injure nerves, blood vessels, or the spinal cord.

Nevertheless, use of a stereotactic IGS procedure presents certain problems and/or complications of its own. For example, one problem associated with common IGS systems is that the interventionalist is forced to continually switch his attention between a display showing the medical diagnostic image and the actual subject where he is working. Physically, over time, the continual switching of attention can lead to eye strain and/or fatigue. Moreover, mentally, it can be quite distracting and/or disruptive to the interventionalist's concentration.

Typical registration methods involve establishing a relationship between the patient space and image space. This is accomplished by the identification of three or more points in each space which define the transformation matrix between patient space and image space. Typically, the points used are anatomical markers, such as, for example, the nasium (bridge of the nose) and ear lobes. Alternatively, adhesive fiducial markers are affixed to the patient prior to imaging and identified by the operator in the diagnostic images. Consequently, the methods employed in the prior art are potentially error prone insomuch as they require the internal anatomy be in the same position relative to the external markers at the time of the diagnostic scan and throughout the registration process and interventional surgical procedure. Since this cannot be guaranteed except in those anatomical locations where the internal anatomy is closely held or fixed in position, such as, for example, in the brain and spinal vertebrae, the prior art has limited use for only a number of interventional procedures.

Moreover, while these markers assist in registering the patient to the electronic images, they do not directly mark anatomical features on the subject. Marking of these anatomical features on the patient is more difficult. This difficulty is compounded because the anatomy of interest is typically below the patient's surface and cannot be seen directly by the surgeon. Changing a viewing angle changes the relative alignment of the surface and underlying planes as well as the perceived alignment of an invasive tool perhaps being used in the procedure.

The present invention provides a new and improved IGS registration technique that overcomes the above-referenced problems and others.

SUMMARY OF THE INVENTION

In accordance with one aspect of the present invention, an image guided surgery system includes a medical diagnostic imager that collects image data from a subject. An image data processor connected to the medical diagnostic imager reconstructs an image representation of the subject from the image data. Ultimately, an image projector depicts the image representation on the subject.

In accordance with another aspect of the present invention, a method for registering a subject in real space with an image of the subject in image space is provided. The method includes obtaining an image of the subject, and projecting the image such that the image is depicted on the subject. Thereafter, at least one of the subject and the depicted image is adjusted relative to the other such that like regions of anatomy coincide.

In accordance with another aspect of the present invention, an image depiction system is provided for use in an image guided surgery system having a medical diagnostic imager for obtaining image representations of a subject. The image depiction system includes an image projector that projects an image onto the subject in accordance with image data received by the image depiction system.

One advantage of the present invention is that subject realignment and registration is able to be accomplished at a higher degree of accuracy.

Another advantage of the present invention is that by bringing the medical diagnostic image into the work area, the interventionalist no longer needs to continuously redirect his vision and/or attention between the surgical site and image display.

Another advantage of the present invention is that it safely brings the image inside the sterile region so that the image can be touched without compromising sterility.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
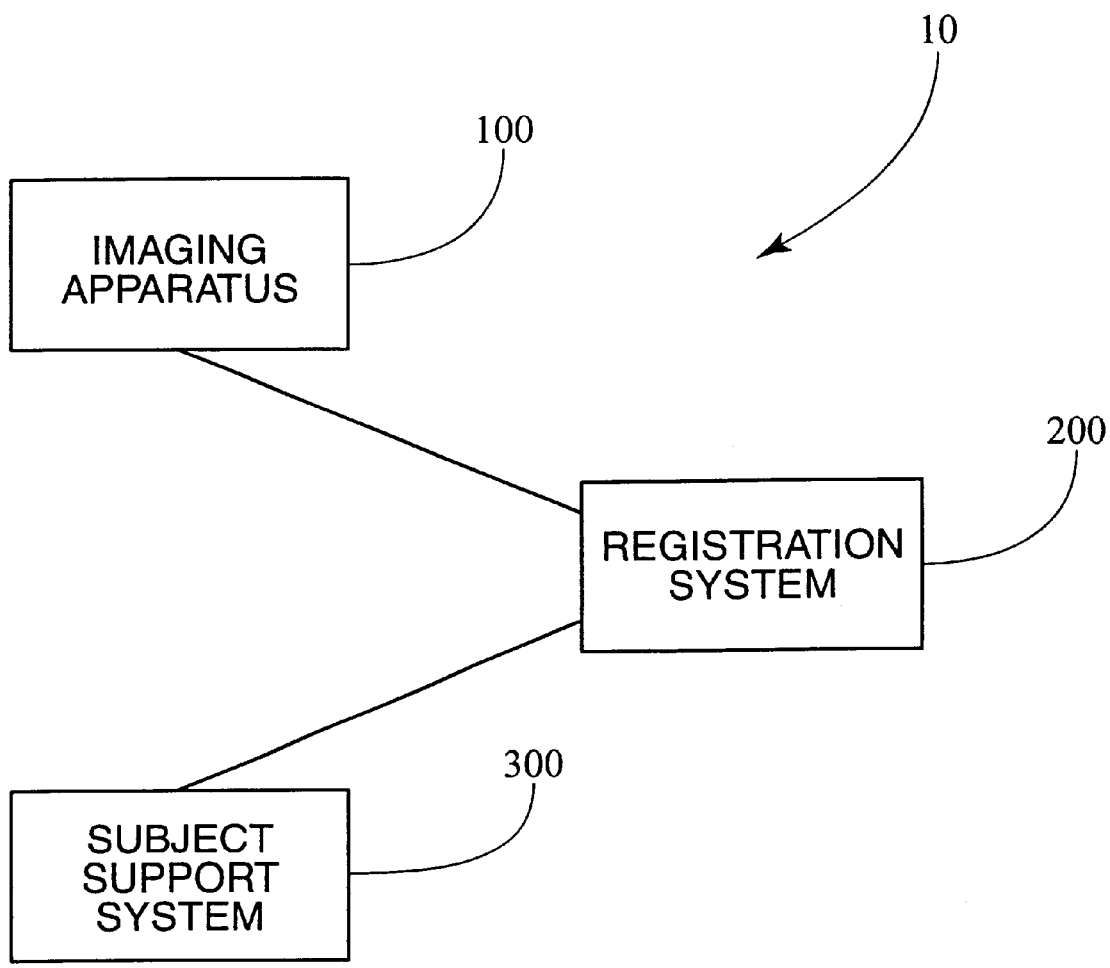
FIG. 1 is a diagrammatic illustration of an IGS system in accordance with aspects of the present invention.

With reference to FIG. 1, an IGS system is indicated generally by reference numeral 10. The IGS system 10 is made up of three main components, namely, an imaging apparatus indicated generally by reference numeral 100, a registration system indicated generally by reference numeral 200, and a subject support system indicated generally by reference numeral 300. The imaging apparatus 100 is employed to obtain non-invasive medical diagnostic images of a subject. The subject support system 300 is employed to receive and/or otherwise support a subject. The registration system 200 is employed to correlate images of a subject's anatomy which are defined in an image space of the imaging apparatus 100 with the corresponding actual anatomy of a subject present within the subject support system 300 defined in real space.

Figure 2:
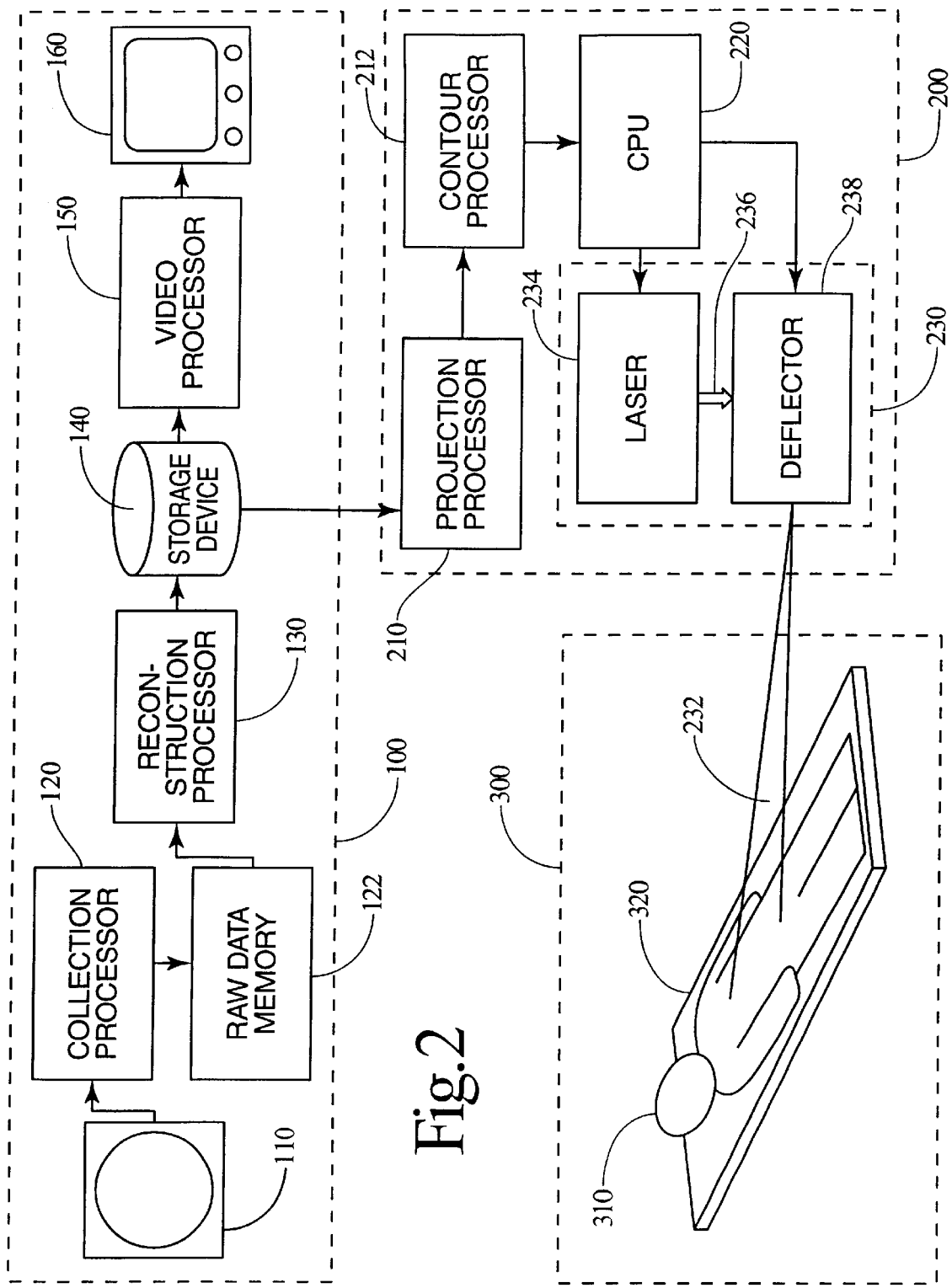
FIG. 2 is a diagrammatic illustration of a registration system for use in connection with an IGS system in accordance with aspects of the present invention; and, FIG. 3 is a diagrammatic illustration of an tracking system for use in connection with an IGS system in accordance with aspects of the present invention.

More specifically, with reference to FIG. 2 and continuing reference to FIG. 1, in use, a subject 310, such as a human patient, animal, phantom, or the like, is received on a top surface 320 of an operating table, couch, or other such subject support. A patient securing structure, such as a head clamp (not shown) and/or patient restraint straps (not shown), securely position or fix at least a portion of the subject to the top surface 320 of the subject support.

Prior to a planned interventional and/or surgical procedure, medical diagnostic images of the subject 310 are obtained in the usual manner via the medical diagnostic imaging apparatus 100. This medical diagnostic imaging apparatus 100 optionally comprises a convention or fluoroscopic x-ray unit, CT scanner, MRI scanner, gamma camera, or other medical diagnostic imaging equipment 110. A data collection processor 120 receives raw image data of the subject's anatomy of interest from the imaging equipment 110. In the CT scanner example, the data collection processor 120 includes an array processor which acquires fan or other like views from the CT scanner. In the MRI scanner example, the data collection processor 120 includes a radio frequency (RF) receiver which acquires signals generated by resonating dipoles in the subject 310 as they decay. The raw image data is stored in a raw data memory 122 and reconstructed into an image representation of the anatomy of interest by a reconstruction processor 130. Employing a reconstruction algorithm appropriate for the imaging modality of the equipment 110 (e.g.; convolution and backprojection for CT and the like; two-dimensional Fourier transform (2DFT) for MRI; and/or other like reconstructions), the reconstruction processor 130 reconstructs an image representation of the subject 310 from the collected data in the raw data memory 122.

Pixels, voxels, or other similar elements of the reconstructed image are stored in a volume image data storage device 140, such as, for example, a magnetic and/or optical disk drive, a designated random access memory (RAM) module, other image memory, or the like. A video processor 150 retrieves slices, projections, 3D renderings, and other image information from the volume image data storage device 140 and appropriately formats an image therefrom for display or depiction on a human viewable display, such as a video monitor 160 or the like. The video display is typically mounted adjacent the surgical area, but outside the sterile region or zone.

The registration system 200 retrieves select image data from the volume image storage device 140 and depicts on the subject 310 a selected image representation, preferably life-size, of the subject's anatomy. In this manner, registration of the subject's anatomy with the depicted image is readily apparent to an interventionalist or other personnel attending to the subject 310. Accordingly, the orientation and position of the subject 310 and the depicted image are adjusted relative to one another such that like regions of anatomy coincide. Optionally, the adjustment is accomplished by appropriately locating the subject 310 on the top surface 320 of the subject support and selectively adjusting the position and orientation of the subject support. In this manner then, a high degree of registration accuracy is achieved insomuch as every surface element of the subject 310 in the area of the depicted image is matched to the corresponding element in the image rather than just a few points represented by anatomical or fiducial markers.

Alternately, the depicted image is adjusted to compensate for the position and orientation of the subject 310. In one implementation, this is accomplished by adjusting the orientation and position of a projector 230 used to depict the image on the subject 310. In another implementation (described later herein), the spatial coordinates of the projector 230, the subject 310, and other system components are monitored or controlled relative to one another or a fix point in space and appropriate corrections are made to the image being depicted so that proper registration is achieved.

More specifically, a selected portion of the image representation is retrieved by an image projection processor 210 from the volume image storage device 140. The image projection processor 210 converts the image data into an appropriate form and format for controlling the projector 230. Preferably, because the image is not being depicted on a flat surface, a contour processor 212 makes corrections to the formatted image from the image projection processor 210 to account for the surface contours of the subject 310 onto which the medical diagnostic image is being depicted. The contour processor 212 accesses the image data stored in the volume image storage device 140 to determine the contour of the surface of the subject 310 onto which the image is to be projected. In a preferred embodiment, the image is being projected onto the skin of the subject 310, in which case, by looking for pixels or voxels in the volume image data characteristic of skin, or preferably, adjoining pixels and voxels indicative of a skin to air transition, the surface contour of the subject 310 is derived. The image contouring processor 212 receives the description of the surface onto which the image is to be projected and warps the formatted image inversely such that it appears undistorted when projected onto the surface of the subject 310.

In operation, a control processor 220 comprising, for example, a central processing unit (CPU) or the like, controls the projector 230 such that it projects and modulates one or more beams of light 232 onto the subject 310 to depict a selected image representation. The selected image representation optionally takes the form of a planar slice or other two-dimensional (2D) view of the subject's anatomy, arrays of planar slices, surface renderings, 3D volume renderings, and the like. For registration purposes, preferably a surface rending is projected.

In a preferred embodiment, the beams of light 232 have one or more wavelengths selected from the visible spectrum.

Alternately, other wavelengths are employed. With an appropriate aid or aids for the wavelength being used, e.g., infrared goggles or the like, these wavelengths are then readily observed.

In a preferred embodiment, the projector 230 is a laser lightshow projector including a laser 234 which selectively generates a beam of low-power laser light 236 directed toward a deflector 238. The beam is low-power in the sense that it is sufficiently weak so as not to harm the subject 310. The deflector 238 preferably comprises one or more motor driven mirrors which selectively reflect the beam of low-power laser light 236 in various directions to depict the desired image representation on the subject 310. Alternately, the deflector 238 is a combination of reflective surfaces and/or lens elements that selectively redirect the beam of low-power laser light 236 as desired for the projection 232 being performed.

Preferably, both the laser 234 and the deflector 238 are controlled by the control processor 220 such that the projector 230 depicts the desired image on the subject 310 in accordance with the image data sampled from the volume image storage device 140. That is to say, in response to the control processor 220, the laser 234 selectively emits the beam of low-power laser light 236 in the direction of the deflector 238. Also in response to the control processor 220, the deflector 238 directs the received laser light onto the subject 310 to form the desired image which corresponds to the image data received by the control processor 220.

Optionally, the projector 230 is a multi-color image projector. In the laser lightshow implementation, the projector 230 employs multiple lasers 234 each generating a different color of low-power laser light to achieve color displays. Moreover, in the case of a laser lightshow projector 230, the control processor 220 preferably comprises a laser lightshow controller, such as, for example, one of the X29 series of laser lightshow controllers made available by MWK Laser Products Inc.

In alternate embodiments, the projector 230 takes the form of a projection television, a backlit liquid crystal display (LCD) device, or similar projection device. Like the multi-laser lightshow projector configuration, these embodiment also optionally produces a color image on the surface of the subject 310.

In addition, the projector 230 optionally provides a large (perhaps, full-color) display of the selected medical diagnostic image on a flat display, such as a screen or wall. In the case of a flat display, no surface contour corrections are carried out by the contour processor 212. Moreover, note that the operations carried out by the image projection processor 210 are optionally combined with and carried out in the reconstruction processor 130 such that the stored image data from storage device 140 is already properly formatted for projection onto the subject 310.

In traditional IGS systems, the image data collected was only viewable on the video monitor 160. Accordingly, the video monitor 160 was placed in a location where the interventionalist and/or attending personnel could view it. However, in a preferred embodiment of the present invention, by bringing the diagnostic image data directly into the work area (i.e., by depicting the desired diagnostic image directly on the subject 310), the interventionalist and/or attending personnel no longer have to use the video monitor 160. Consequently, in one alternate embodiment, the video monitor 160 is freed for use as an auxiliary monitor that is optionally positioned for optimal viewing by observers, such as medical students, observing physicians, etc. Having the video monitor 160 so oriented also keeps the potentially distracting observers at a distance so that interference with procedures being performed is minimized. Of course, alternately, the video monitor 160 may still be employed by the interventionalist as a secondary source of medical diagnostic image information.

Additionally, IGS system 10 of the present invention aids the interventionalist in other ways. By bringing the diagnostic image data directly into the work area, the interventionalist and/or attending personnel are able to navigate or otherwise study a subject's anatomy without having to continuously redirect their vision and/or attention between a procedure site and an image location. That is to say, the procedure site and image location coincide. Accordingly, potential distraction or loss of place, eye movement and/or strain, fatigue, and the like are minimized.

The IGS system 10 in accordance with embodiments of the present invention finds use in various procedures and applications. For example, in an alternate embodiment or application, a set of diagnostic images are taken at different portions or time of a respiratory or other biological cycle. The depicted images projected onto the subject 310 are then alternated to compensate for the biological cycle. Optionally, in the case of a respiratory cycle, the subject 310 is given breathing guidance to match his respiratory cycle to a cine loop. Alternately, the speed of the cine loop is adjusted to match the monitored biological cycle of the subject 310.

In another exemplary embodiment or application, the IGS system 10 is useful in the performance of a needle biopsy. As the needle biopsy is being performed, images of interior planes perpendicular to the trajectory of a biopsy needle are projected onto the subject 310 at least in the area surrounding the biopsy needle. The interventionalist is able then to "zoom down through the subject's anatomy" right at the biopsy site with the current projected plane corresponding to the current depth of the biopsy needle.

Figure 3:
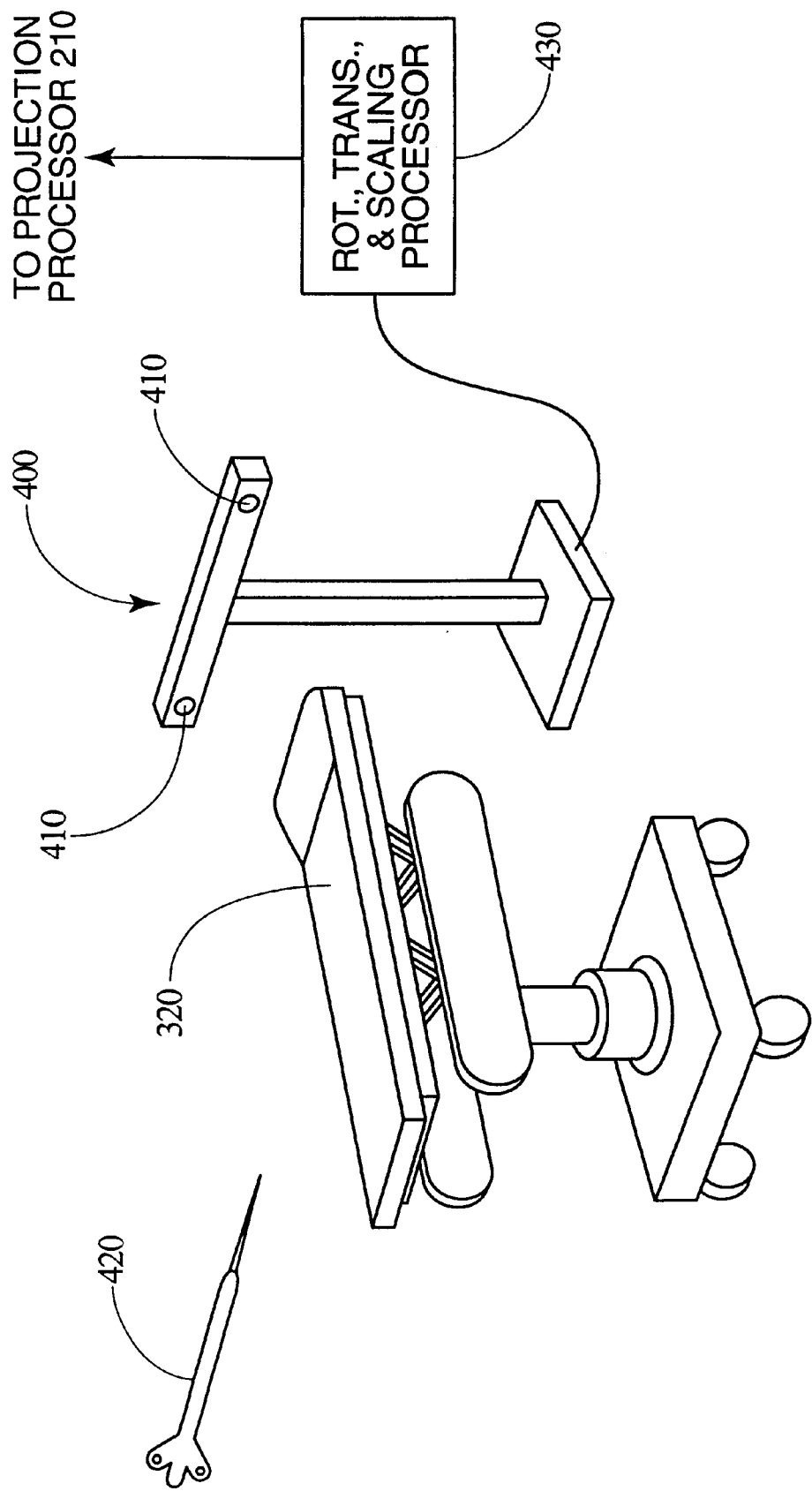

With reference to FIG. 3 and continuing reference to FIGS. 1 and 2, in a preferred embodiment, a tracking system includes a detection unit 400 having receivers 410, such as CCD arrays, IR cameras, light sensitive diodes or the like. Alternately, the receivers 410 sense or detect other types of radiant energy, such as ultrasound, x-ray, radio waves, magnetic waves, or the like. The receivers 410 detect radiation of the selected type received from passive or active emitters transmitting the same. In this manner, the detection unit 410 resolves the spatial location of the emitters. The emitters are affixed to the different components to track their location in real space. For example, they are optionally affixed to the patient support or top surface 320 thereof (hence location of the subject 310 thereon is tracked), to the projector 230, or to a surgical tool, such as the illustrated wand 420, a biopsy needle, a needle guide, etc. Optionally, each of the aforementioned components are connected to the imaging equipment 110 via adjustable mechanical linkages and calibrated encoders indicate their position relative to a fix point, e.g., a geometric center of the imaging equipment 110. In this manner, their relative orientations and positions are determined.

In a preferred embodiment, a rotation, translation, and scaling processor 430 determines appropriate corrections to be applied to the selected image for the position and orientation of the subject 310. That is to say, from this information (i.e., the positions of the components), the translation, rotation, and scaling processor 430 generates adjustments employed by the projection processor 210 such that the image being projected is depicted in the proper size and rotation on the region of interest of the subject 310. This eliminates manual adjustment of the projector 230 or the subject 310 for registration purposes. Moreover, optionally, by tracking a surgical tool (e.g., the wand 420) in real space (which is registered with the image space) a graphic representation of the surgical tool is mapped to image space where it is visualized either via the video monitor 160 or otherwise.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An image guided surgery system comprising:
    a medical diagnostic imager that collects image data from a subject;
    an image data processor connected to said medical diagnostic imager, said image data processor reconstructing an image representation of the subject from the image data;
    contouring means for adjusting the image representation so that it is substantially undistorted when projected onto a contoured surface of the subject's anatomy; and,
    an image projector that projects the image representation on a surface of the subject's anatomy, wherein that which is depicted in the image representation includes anatomy of the subject other than the anatomy on which the image representation is being projected.

2. The image guided surgery system according to claim 1, wherein the image projector includes:
    a light source which produces a beam of light; and
    a deflector which redirects the beam of light in accordance with the image representation being depicted.

3. The image guided surgery system according to claim 1, wherein the image projector is selected from a group consisting of a laser lightshow projector, a projection television, and a backlit liquid crystal display device.

4. The image guided surgery system according to claim 1, wherein the image projector is a multi-color projector which depicts the image representation on the subject in multiple colors.

5. An image guided surgery system comprising:
    a medical diagnostic imager that collects image data from a subject;
    an image data processor connected to said medical diagnostic imager, said image data processor reconstructing an image representation of the subject from the image data;
    contouring means for adjusting the image representation in accordance with a contoured surface of the subject's anatomy when projected onto that contoured surface;
    a laser which produces a beam of laser light;
    a deflector which redirects the beam; and,
    a control processor which regulates production of the beam by the laser and controls redirection of the beam by the deflector such that the image representation is visualized on the subject.

6. The image guided surgery system according to claim 5, wherein the control processor comprises a laser lightshow controller.

7. An image guided surgery system comprising:
    an image projector that depicts on a subject an image representation of the subject which is reconstructed from image data collected from the subject; and,
    a contour processor that corrects the image representation such that surface contours of the subject are accounted for when the image representation is depicted thereon by the image projector.

8. The image guided surgery system according to claim 7, wherein the contour processor determines surface contours of the subject from the image representation.

9. A method for registering a subject with an image of the subject, the method comprising:
    (a) obtaining an image of the subject;
    (b) processing the image to adjust it for contours on a surface of the subject where the image is to be projected;
    (c) projecting the image onto the subject; and,
    (d) adjusting at least one of the subject and the image relative to one another to bring like regions of anatomy into coincidence with one another.

10. A method for conducting image guided medical procedures, wherein the method comprises:
    (a) obtain an image of a subject;
    (b) processing the image to account for contours on a surface of the subject; and,
    (c) protecting the processed image onto the surface of the subject.

11. The method according to claim 10, wherein the step of processing further comprises:
    determining the contours of the surface from the image of the subject.

12. The method according to claim 10, wherein step (b) further comprises projecting the image in multiple colors such that the image is depicted on the subject in multiple colors.

13. The method according to claim 10, wherein the image depicts anatomy which lies a selected depth beneath the surface upon which the image is being projected.

14. The method according to claim 13, wherein the selected depth corresponds to a depth at which a medical instrument is inserted into the subject.

15. The method according to claim 13, further comprising:
    (d) monitoring a position of a medical instrument; and,
    (e) changing the selected depth in response to changes in the position of the medical instrument.

16. The method according to claim 15, wherein the selected depth corresponds to a depth at which the medical instrument is inserted into the subject.

17. A method for conducting image guided medical procedures comprising:
    (a) obtain an image of a subject which is to be depicted on the subject;
    (b) processing the image to adjust it for contours on a surface of the subject where the image is to be depicted;
    (c) modulating a beam of laser light in accordance with the image being depicted; and,
    (d) deflecting the modulated beam such that it traces a path on the subject in accordance with the image being depicted.

18. In an image guided surgery system employing diagnostic medical image data from a subject, an image depiction system comprising:
    an image projector that projects an image generated from the image data onto a surface of the subject, said image including anatomy which does not correspond to the surface on which the image is being projected; and,
    a image correction processor that adjusts the image to compensate for the contours of the surface on which the image is being projected.

19. An image depiction system comprising:
- an image projector that projects an image onto a subject in accordance with image data acquired from the subject; and,
- a data processor that applies corrections to the image data such that surface contours of the subject are accounted for when the image is projected onto the subject.

20. The image depiction system according to claim 18, wherein the image projector is selected from a group consisting of a laser lightshow projector, a projection television, and a backlit liquid crystal display device.

21. The image depiction system according to claim 18, wherein coincidence of corresponding features in the depicted image and the subject determine registration of the image with the subject.

* * * * *